United States Patent [19]

Tayebi et al.

[11] Patent Number: 5,225,158
[45] Date of Patent: Jul. 6, 1993

[54] APPARATUS FOR COLLECTION AND DECONTAMINATION OF HAZARDOUS AND INFECTIOUS WASTE AND CARRIER AIR

[76] Inventors: Amad Tayebi, 5 Sequoia Rd., Westford, Mass. 01886; Noble Gabriel, 13 Copley Dr., Andover, Mass. 01810

[21] Appl. No.: 380,008

[22] Filed: Jul. 14, 1989

[51] Int. Cl.⁵ .............................. A61L 9/00
[52] U.S. Cl. ......................... 422/4; 422/28; 422/33; 422/120; 55/256
[58] Field of Search .......... 422/4, 28, 33, 120, 422/122, 168; 461/119.1; 55/256; 433/91-96

[56] References Cited

U.S. PATENT DOCUMENTS

| | | | |
|---|---|---|---|
| 4,172,865 | 10/1979 | Steier | 261/119.1 |
| 4,226,590 | 10/1980 | Hofmann | 433/91 |
| 4,293,300 | 10/1981 | Cattani | 433/92 |
| 4,589,442 | 5/1986 | Ernryd | 433/92 |
| 4,731,224 | 3/1988 | Kawashima | 422/122 |
| 4,824,363 | 4/1989 | Abthoff et al. | 422/4 |
| 4,874,404 | 10/1989 | Boswell | 55/244 |
| 4,963,094 | 10/1990 | Meyer | 433/95 |

FOREIGN PATENT DOCUMENTS 8810102 12/1988 World Int. Prop. O. .......... 433/95

Primary Examiner—Robert J. Warden
Assistant Examiner—T. A. Trembley
Attorney, Agent, or Firm—Joseph E. Funk

[57] ABSTRACT

A waste collection container fitted with an inlet point and an outlet point is used for receiving contaminated carrier air from a medical suction procedure. Heavier solids and liquids are collected within the waste collection container by gravitational precipitation. The carrier air now containing only aerosol contaminants is then bubbled through a disinfecting bath to sterilize the carrier air before it is exhausted into the immediate indoor environment or the outdoor atmosphere. An activated charcoal filter is then used to remove odors from the sterilized carrier air. An input and exit port of the waste collection container are initially sealed and are punctured by manually operated actuator apparatus to permit carrier air to flow through the container and the disinfecting bath. When the waste collection container is full, before removal another actuator is manually operated to discharge the disinfecting bath into the precipitated fluids and solids in the container to thereby sterilize them.

25 Claims, 2 Drawing Sheets

APPARATUS FOR COLLECTION AND DECONTAMINATION OF HAZARDOUS AND INFECTIOUS WASTE AND CARRIER AIR

FIELD OF THE INVENTION

This invention is in the field of collection and sterilization of suction collected infectious waste, and to the treatment of the suction carrier air to prevent the contamination of the surrounding environment.

BACKGROUND AND OBJECTIVE OF THE INVENTION

In hospital operating rooms, emergency treatment rooms, veterinaries, mortuaries, pathology laboratories, physician's offices and dentist's offices, millions of suction procedures are performed annually. Such suction operations or procedures are conducted for removal and/or collection and disposal of body fluids such as blood, urine, saliva, body treatment fluids, body tissues, organs, organ sections or portions, bone chips and contaminated vapors or fumes generated from cauterization or laser beam surgical procedures.

In all such suction operations, a pressure drop (vacuum) between the point of suction and the point of collection and/or precipitation is utilized in order to induce the flow through conduits from the suction point towards the collection point. When such vacuum induced flow for collection and/or precipitation of fluids, organs and vapors is conducted, a potential hazard arises since the carrier air (exhausted beyond the collection/precipitation point) may be contaminated with harmful pathogenic bacteria, germs, viruses, particles, fluid mists, vapors, and gases. When the carrier air is exhausted in a limited or finite space, such as within a dentist's or physician's office, or a small clinic, the immediate surrounding environment will be contaminated with such hazardous contaminants. When the carrier air is collected in a common or central location, for example in hospitals, it is usually exhausted outdoors, thus causing a potential outdoor contamination hazard, particularly in the immediate neighborhood.

Presently, suction procedures are conducted so that fluids, tissue and vapors are collected at a first collection point or container within the room at which the surgical or medical procedure is conducted. The precipitation and collection of the fluids and tissues is usually done in clear plastic canisters. A typical collection canister is of a truncated conical shape, with approximately 5 inches upper end diameter, 3½ inches lower end diameter and 12 inches height. Such collection canisters are fitted with inlet and outlet hose connection nipples, and a cup shaped float which acts as an automatic shut-off valve and closes the outlet flow point when the level of material in the cannister reaches a certain point. This eliminates any overflow problems. When shut-off occurs the pressure drop or vacuum necessary for the suction process is stopped and the collection canister is disconnected and either emptied or replaced with an empty container.

The majority of prior art collection canisters utilize only gravity for precipitation and collection of fluid and tissue, thus permitting contaminated or hazardous fumes, mists and vapors to be exhausted where they contaminate the indoor environment or the outdoor atmosphere. More advanced types of prior art collection canisters utilize a highly efficient filtration system that traps up to 99.9% of aerosolized microorganisms and particulate matter in order to prevent airborne contamination. Unsolved problems still exist with such prior art systems.

A first problem is that even 0.1% or less of aerosolized microorganisms escaping through such filtration systems may be sufficient to contaminate the intermediate exhaust air conduits, and thus pose a contamination hazard for the indoor environment and/or the outdoor atmosphere. Further, since viruses range in size from 100 to 2000 Angstroms, it is virtually impossible to achieve complete filtration of the viruses from the carrier air before the carrier air is delivered to the intermediate exhaust air conduits.

A second problem is that bacteria trapped in the highly efficient filtration system can multiply at a high rate due to moisture in the filter resulting from trapping organic fluids such as blood and saliva. In effect, the filter acts as a favorable medium for the bacteria to multiply and subsequently escape into the intermediate exhaust air conduit as suction continues.

A third problem is that the contents of the collection cannisters are highly contaminated and disposal of the container poses a contamination hazard to the soil of its disposal site, and to the atmosphere surrounding the disposal sites.

Accordingly, a need exists for medical waste collection apparatus to collect and precipitate fluids, tissue, mists and vapors in such a manner that nothing harmful is allowed to escape to either the indoor environment or the outdoor environment, before or after disposal.

A need also exists for means in medical waste collection apparatus to disinfect the medical waste contents of collection containers in order to make the disposal of such containers non-contaminating to both the soil of the disposal site and to the atmosphere surrounding the site.

There is also a need for means in medical waste collection apparatus to disinfect suction carrier air passing therethrough prior to its exhaust to the indoor or outdoor environment.

SUMMARY OF THE INVENTION

The above described needs of the prior art are met by the present invention which is suction activated medical waste collection apparatus used to collect and precipitate fluids, tissue, mists and vapors resulting from medical and dental procedures and disinfecting same in such a manner that nothing harmful is allowed to escape to either the indoor environment or the outdoor environment, before or after disposal. In addition, suction air passing through the collection apparatus is sterilized before it is exhausted from the apparatus.

The medical waste collection apparatus has a waste collection container used as a first collection point for receiving medical suction procedure carrier air and the fluids, tissue, mists and vapors carried thereby. Within the first collection point container gravitational precipitation of relatively heavier fluids, tissues, solids, and other contents of the carrier air occurs. Means are provided for sterilization of the carrier air passing through the apparatus prior to its exhaust from the apparatus. Another means is also provided for sealing a full collection container and disinfecting the contents of same prior to its disposal. The result is that in essence no hazardous contaminants of any form are allowed to escape from the apparatus into the immediate indoor environment or to the outdoor atmosphere before or after disposal of a full collection container.

BRIEF DESCRIPTION OF THE DRAWING

The present invention will be better understood upon reading the following specification in conjunction with the drawing in which.

DETAILED DESCRIPTION OF THE INVENTION

Figure 1:
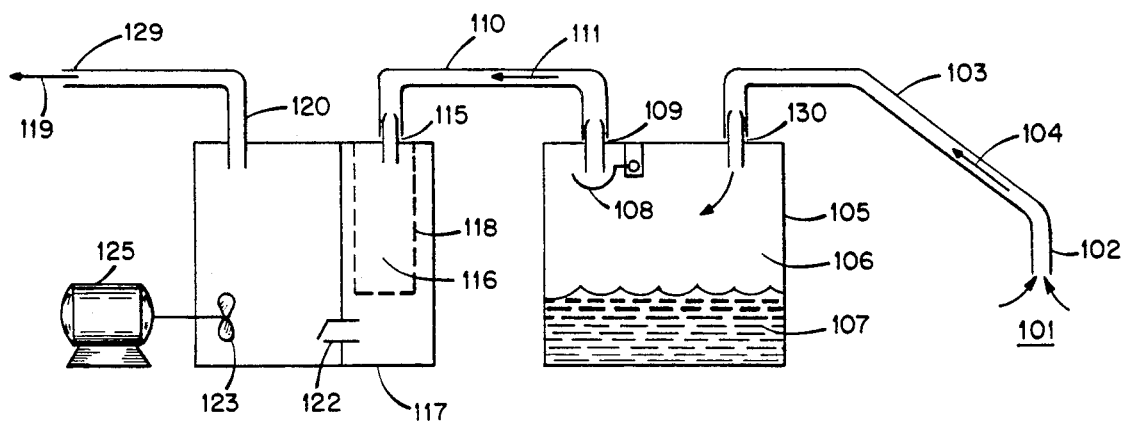
FIG. 1 is a block diagram of a prior art waste collection apparatus showing flow of carrier-air from a suction point into a first collection container, through an intermediate exhaust air conduit, to a vacuum source wherein the intermediate exhaust air is subsequently pressurized in order to be discharged into the surrounding environment.

FIG. 1 shows a block diagram of a typical prior art suction activated, waste collection apparatus. Very briefly, a suction source 117 is connected to a waste collection container 105 to which is also connected a carrier air conduit 103. The suction created by suction source 117 causes air to be drawn up into waste conduit 103, pass through waste collection container 105, and suction source 117 before being exhausted via exhaust air conduit 120 back to the environment. In operation waste matter is drawn up by the suction air being drawn up into carrier air conduit 103 and enters waste collection container 105 where it is deposited as precipitated fluids and solids 107. The suction air, which will still have aerosol particles exits collection container 105 and passes through and intermediate air conduit 110 to the suction source 117 where it passes through a filter 118 to remove aerosol or other fine particles. The filtered air finally exits the apparatus via exhaust air conduit 120.

More particularly, suction of contaminated fluids, solids, vapors, and gases starts at point 101 which is the suction end 102 of a carrier air conduit 103. As the pressure Ps inside the carrier air conduit 103 is lower than the atmospheric pressure Pa surrounding suction point 102, due to the action of suction source 117, airborne contaminated fluids, solids, gases, and vapors flow into and through conduit 103 to waste collection container 105. Container 105 is fitted with an inlet point 130 which receives carrier air conduit 103 and directs the carrier air 104 and its contaminated contents into the interior 106 of waste collection container 105. Gravity causes the contaminated fluids and solids transported by carrier air 104 to precipitate inside waste container 105. The carrier air moves through container 105 towards its exit point 109 to which is connected intermediate exhaust air conduit 110.

The carrier air exiting waste collection container 105 via exit port 109 still contains contaminated germs, viruses, mists, vapors, fine particles and gases due to the aerosolized nature of the mixture.

As the level of precipitated fluids and solids 107 collected in waste collection container 105 rises, it reaches a level where a full level shut-off valve or float 108 is pushed upward thus closing exit point 109. This causes the pressure drop which induces the suction at suction point 101 to cease. When this occurs, the attending nurse or operator disconnects carrier air conduit 103 and intermediate exhaust air conduit 110 from entry and exit points 130 and 109, respectively. Waste collection container 105 is then replaced with an empty container and the suction process is resumed.

The intermediate exhaust air 111 flowing through intermediate exhaust air conduit 110 enters a pressure drop (vacuum) generation source 117 via its entry point 115. Vacuum generation source 117 may be of a localized type, such as a small vacuum pump, or may be of a centralized type such as a central vacuum source in a hospital. In all cases intermediate exhaust air 111 is directed into the interior 116 of a porous filter or particulate collection bag 118 to remove the contaminated aerosol. Typically, the filtered intermediate exhaust air 111 passes through a one-way air flow valve 122 and is then pressurized to a pressure Pe (where Pe>Pa) by air compressing means 123. Compressing means 123 is driven by mechanical power input source 125 in FIG. 1. The filtered intermediate exhaust air 111 subsequently passes through final exhaust air conduit 120 and is exhausted as final exhaust air 119 into the surrounding environment.

A number of relative magnitude relationships has to be maintained between the air pressures at the various points in suction system shown in FIG. 1 typically as follows: Pa>Ps, Pv<Pc<Ps, Pe>Pv and Pe>Pa, where Pa is the atmospheric pressure surrounding the suction point, Ps is the pressure inside of the carrier air conduit 103, Pc is the pressure inside of first collection point container 105, Pv is the pressure inside of porous filter 118 and Pe is the compressed final exhaust air pressure.

Figure 2:
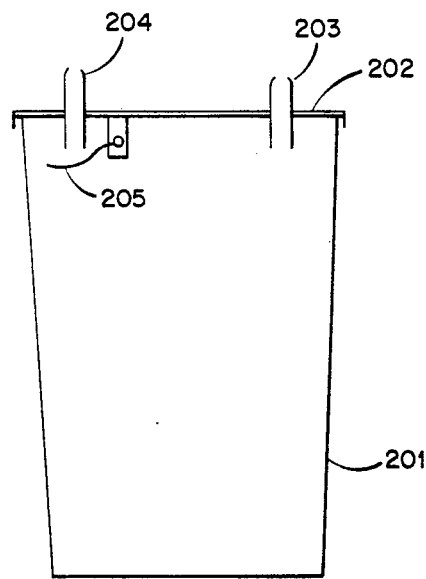
FIG. 2 shows a waste collection container of prior art waste collection apparatus.

FIG. 2 shows a typical prior art waste collection container 201 with a removable lid 202, inlet port 203, outlet port 204 and full level shut-off valve 205. In some instances, contents of container 201 are emptied into sewer lines. Due to the infectious nature of the contents of container 201, such practice may contaminate sewer treatment facilities and subsequently drinking water supplies and/or ocean or river waters.

Figure 3:
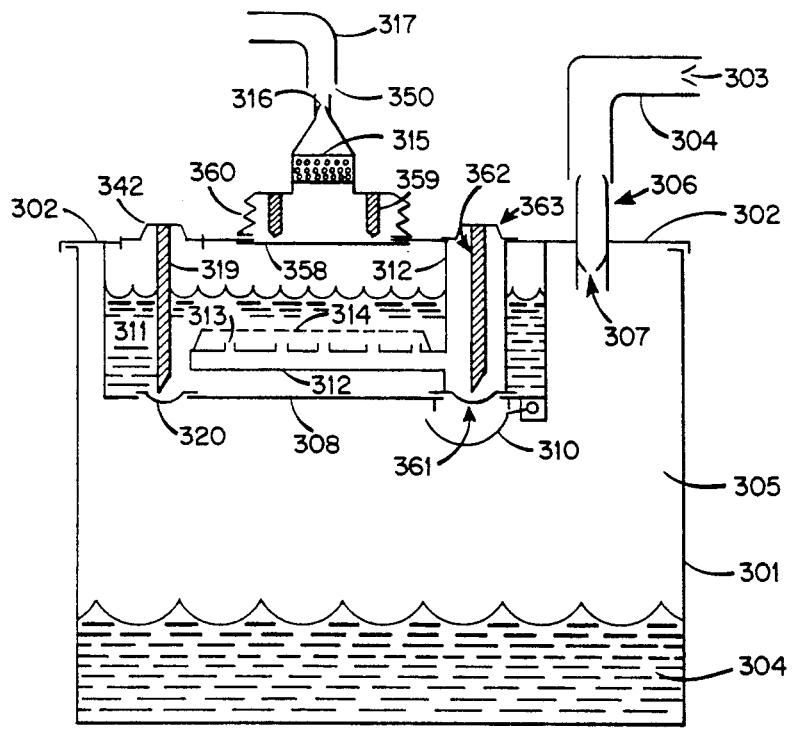
FIG. 3 shows a waste collection container fitted with our novel means for disinfecting suction carrier air and suction collected waste in accordance with the teaching of the present invention.

As shown in FIG. 3, a waste collection container 300 is equipped with disinfectant apparatus in accordance with the teaching of the present invention to decontaminate carrier air being sucked into container 300 via conduit 304. Also, a means is provided to disinfect all the contents of waste collection container 300 prior to its disposal. Waste collection container 300 may be manufactured of an impermeable, preferably transparent or translucent container body 301. Container body 301 is preferably positioned in a vertical orientation. Container body 301 is sealed with a lid 302 which is preferably hermetically sealed to body 301, but which may be removable. The hermetic seal can be achieved by an adhesive, ultrasonic, heat or other means.

Lid 302 has an entry port 306 which preferably has a ridged tapered outer diameter so that it may accept a variety of sizes of conduit 304 with an effective seal. Entry port 306 is fitted with a one way valve 307 allowing air to flow only into the interior of body 301 via port 306. Contaminated carrier air 303 is transported through conduit 304 into the interior 305 of waste collection container 301 via port 306.

In accordance with the teaching of the present invention waste collection container 300 is fitted with a decontamination/disinfecting chamber 308 which is preferably located within the interior of body 301 under lid 302. Alternatively, some of the components of decontamination/disinfecting chamber 308 may be located within the interior of container 300 while other components may be located above lid 302 exterior to waste collection container 300. Decontamination chamber 308 has an entry port 309 which is initially sealed with a membrane or cover 361. Membrane 361 has a full level shut off lid 310 adjacent to it which is similar in concept, function and performance to prior art full level shut off lids.

Figure 3A:
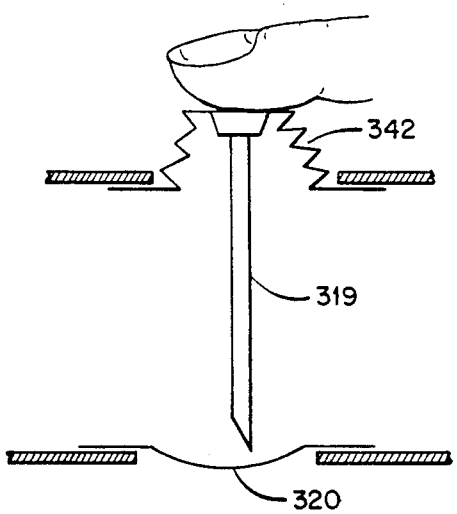
FIG. 3A shows an embodiment of means for disinfecting collected waste in the collection container after it is full.

When suction is to be conducted, a needle or pin element 362 is pushed down to puncture or remove membrane or cover 361. This is accomplished by pressing down on activator 363 which is preferably alike activator 342 which is described further in this specification and is shown in detail in FIG. 3A. As contaminated carrier air 303 enters into the interior 305 of container 301 via entry port 306, its heavy fluid particles, tissues, and any other solids 340 are precipitated at its bottom. Subsequently, fluid mist particles, light and/or fine solid particles and fumes continue to be carried by contaminated carrier air into decontamination chamber 308 via its entry port 309.

In the preferred embodiment of the invention, a membrane or cover 358 separates the interior of decontamination fluid bath 311 from exit port 350. Further, a bellows-shaped actuator 360 is located between filter 315 and membrane or cover 358 a shown in FIG. 3. Needles or pin elements 359 are provided above membrane or cover 358. When suction is to be conducted, actuator 360 is manually depressed to thereby cause pin elements 359 to puncture or remove membrane or cover 358 and thus permit flow of carrier air to exit port 350.

In accordance with the teaching of the present invention contaminated carrier air is decontaminated/disinfected by being passed through a decontamination medium 311. Such a decontamination medium 311 may be a disinfecting fluid such as alcohol, household bleach, or a household cleaners such as LYSOL ™. Alternatively, instead of a disinfecting fluid the carrier air may be passed through a disinfectant-treated porous medium such as a fibrous medium or open cell polymeric foam. Decontamination may also be conducted by passing contaminated carrier air through heated channels or heated porous media in order to kill the germs, viruses or microorganisms in the carrier air. Alternatively, carrier air may be decontaminated by ultraviolet rays, gamma radiation or microwave heating.

As shown in FIG. 3 decontamination chamber 308 comprises a decontamination fluid bath 311. Contaminated carrier air 303 is fed to the bottom of bath 311 through conduit 312 because of the pressure drop between entry port 306 of container 300 and exit port 350 of decontamination chamber 308. Conduit 312 may be connected to entry port 309 or may form a unitary integral conduit with entry port. The contaminated carrier air 303 flows through conduit 312 to the bottom of bath 311 and enters bath 311 via a plurality of exit points 313. Carrier air 303 bubbles up through decontamination liquid 341 and is thereby disinfected. Exit points 313 may comprise one large opening, though preferably they comprise a plurality of small openings in order to decrease the air bubble size so that more effective decontamination may be achieved.

To further reduce the air bubble size and hence achieve a more thorough decontamination of carrier air in the bubbles, decontamination chamber 308 is preferably fitted with at least one layer of bubble size reduction means, such as fine mesh 314 which is located above exit points 313 and below the level of decontamination liquid 341. As contaminated air bubbles pass through bubble size reduction means 314, their size is reduced and thus a more thorough decontamination and precipitation of fluid mists and fine solid particles is achieved.

Size reduction means 314 may also be of a fibrous nature, an open cell polymeric foam, a metal wire mesh or some other porous solid. Also, size reduction means 314 may be wrapped around conduit 312 over exit points 313. Further, in another embodiment of the invention, the function of bubble size reduction means 314 may be achieved by fitting exit points 313 with porous exhaust plugs (not shown). Such porous exhaust plugs may be of a polymeric fibrous or open cell foam nature, or may be a porous metallic material such as a sintered metal exhaust mufflers widely utilized in pneumatic applications.

As carrier air travels to above the surface of disinfectant liquid 341 its decontamination is virtually completed. However, in order to insure that treated air exiting through exit port 350 is thoroughly cleaned, filtered and deodorized, it is preferred that a particulate and odor removal filter 315 be located between the top of liquid 341 and exit port 350. Filter 315 may be a particulate filter or a vapor or gas absorption filter, such as an activated charcoal cartridge, or a combination thereof. Filter 315 may also be of a multi-layer structure, preferably with spaced apart layers in order to prevent inter-layer wicking and subsequent clogging. Such a multilayer filter is preferably constructed such that the upstream layers are coarser in structure than the downstream layers in order to provide a depth filter with a higher capacity and a lower pressure drop. Exit port 350 is also fitted with a one way valve 316 that is in a normally closed position when the unit is not in use.

Figure 4A:
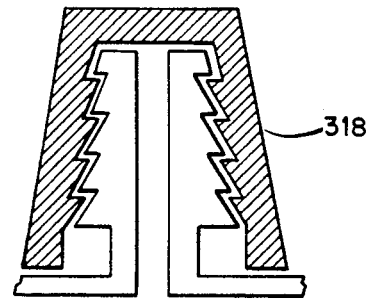
FIGS. 4A and 4B show cross sectional views of entry and exit ports and a matching locking cap for closing same for the waste collection container.

In actual use, the level of precipitated fluids and solids 340 reaches a point where full level shut off lid 310 closes entry port 309 of decontamination chamber. When this occurs, suction thereby ceases and a high pressure drop is experienced by the vacuum generating unit. A pressure sensing means (not shown) may be used to actuate a full container alarm. A nurse or operator then replaces waste collection container 300. When this is done input conduit 304 and output conduit 317 are disconnected from entry port 306 and exit port 350 respectively. In accordance with the present invention, it is preferred that exit port 350 and entry port 306 be sealed. This may be done in many ways including heat sealing, adhesive application, or other methods readily available and proven in the prior art. However, in a hospital setting, it is preferred to provide a matching locking cap, preferably made of a flexible plastic such as polyurethane or flexible vinyl to permanently seal entry port 306 and exit port 350. An example of such a locking cap is molded cap 318 which is shown in FIG. 4A. The sealing cap 318 is preferably fitted with a tapered sealing tip 390, also shown in cross-sectional view in FIG. 4A, which is self explanatory.

Figure 4B:
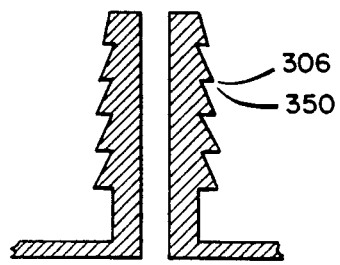

As shown in cross-sectional view in FIG. 4B, entry port 306 and exit port 350 are shaped in a ridged tapered outer diameter configuration with a truncated Christmas tree-like shape to interlock with locking cap 318 to create an effective seal. Another benefit obtained by utilizing such a locking cap system is that inlet and outlet ports 306 and 350 will not be inadvertently opened while in transit.

To further treat and disinfect the precipitated fluid and solids 340 collected in a filled and sealed waste collection container 300, a discharge means is provided for transferring the decontamination/disinfectant fluid 311 contained in disinfectant chamber 308 to mix with the precipitated fluids and solids 340 collected in the interior of waste collection container 301. To accomplish the mixing a puncturing needle or pin 319 is fitted to the underside of a specially marked actuator 342 which is shown in greater detail in FIG. 3A. As shown therein, the bottom of decontamination fluid bath 311 has a thin, weak section 320. Needle or pin 319 is permanently attached to the underside of actuator 342. As actuator 342 is manually depressed pin 319 is pushed down and punctures the bottom of bath 311 at point 320. When this happens the disinfecting fluid in bath 311 flows downward into the interior 305 of waste collection container 300 where it mixes with precipitated fluids and solids 340 and disinfects same.

Thus, the vacuum source, the intermediate exhaust-air system and conduits and the surrounding environment are all protected from contamination. Further, the disposable waste collection container is internally disinfected/decontaminated so that its disposal does not pose any infectious or contamination threat to the environment.

In an alternative embodiment of the present invention, disinfection of carrier air may be carried out by being passed through a fibrous medium saturated with disinfecting fluid or medium (not shown), rather than by being bubbled through disinfecting liquid 341. Contaminated carrier air 303 may also be disinfected by being passed through a heated medium (not shown) so that germs and viruses are killed prior to exiting via exit port 350.

In a retrofitting embodiment of the present invention, a cartridge-like unit may be connected to outlet port 204 of waste collection canister 201 in FIG. 2. The cartridge-like unit contains elements similar to those contained in decontamination chamber 308 including a particulate and/or odor filter 315.

As mentioned previously, in yet another embodiment of the present invention, heat may be used to decontaminate the contents of intermediate exhaust air 111, for example by passing it through a high temperature porous heated medium unit (not shown). Such a heated air disinfecting unit may preferably be connected directly to exit port 109 or be located at some point between exit port 109 and final exhaust air exit point 129. More particularly, such a high-temperature air disinfecting unit comprises a heating element and a heated fibrous web, preferably made of ultra fine stainless steel fibers. As contaminated air enters into the interior of the disinfecting unit, and then passes through its heated porous filtration system, viruses, bacteria and other pathogenic contaminants are killed.

Alternatively, decontamination chamber 308 may be fitted with means for thermally disinfecting exhaust air (not shown) prior to exiting via exit port 350. More particularly, carrier air exit points 313 may be fitted with heated porous plugs, for example similar to those widely known and used as exhaust mufflers for pneumatic applications.

Although the preferred embodiment of the invention and some alternative embodiments of the invention have been described hereinabove, it should be understood that those skilled in the art may make numerous changes without departing from the spirit and scope of the invention.

What is claimed is:

1. In a decontamination apparatus used with a suction source which creates suction that causes a suction air flow into and through a suction pickup device which picks up waste matter that is deposited in said decontamination apparatus before said suction air flow is exhausted into the surrounding environment, the improvement comprising:

a closed container having an input port and an exhaust port, said exhaust port being coupled to said suction source and said suction pickup device being coupled to said input port, said suction air flow entering said closed container via said suction pickup device and said input port, and exiting said closed container via said exhaust port, said closed container collects said waste matter that is drawn into said closed container via said input port by said suction air flow passing through said suction pickup device; and a first disinfectant means located inside said closed container adjacent to said exhaust port which sterilizes said suction air flow exiting said closed container via said exhaust port, said suction air flow passing through said first disinfectant means after said suction air flow enters said closed container and said waste matter is collected in said closed container.

2. The decontamination apparatus in accordance with claim 1 further comprising:

filter means located adjacent to said exhaust port through which sterilized suction air flow exiting said closed container passes to remove particulate matter and odors from said sterilized suction air flow before it is exhausted into the surrounding environment.

3. The decontamination apparatus in accordance with claim 1 wherein said first disinfectant means comprises a first disinfectant bath, and further comprising:

a tank means for containing said first disinfectant bath, said first disinfectant bath providing for sterilization of said suction air flow passing through said closed container before said suction air flow is exhausted from said closed container into the surrounding environment.

4. The decontamination apparatus in accordance with claim 3 wherein said tank means has a drain that is capable of opening when said closed container is full of waste matter to drain said first disinfectant bath into said waste matter to disinfect same.

5. The decontamination apparatus in accordance with claim 3 further comprising:

a pipe means located in the bottom of said tank means through which said suction air flow passes when said suction source is connected to said exhaust port and said suction pickup device is connected to said input port, said pipe means having an end open to said closed container above said collected waste matter, and having at least one exit port through which said suction air flow passes into said first disinfectant bath to initially be broken up into a first plurality of bubbles; and screen means above said pipe means located through which said first plurality of bubbles pass to be broken up into a larger number of fine bubbles, said pipe means and said screen means being located in said first disinfectant bath, thereby permitting said larger number of fine bubbles to pass up through said first disinfectant bath to sterilize said suction air flow.

6. The decontamination apparatus in accordance with claim 1 further comprising:

a first one-way valve located adjacent said input port for permitting said waste matter and said suction air flow to enter said closed container via said input port while preventing anything from exiting said closed container via said input port; and a second one-way valve located adjacent said exhaust port for permitting said sterilized suction air flow to exit said closed container via said exhaust port, while preventing anything from entering said closed container via said exhaust port.

7. The decontamination apparatus in accordance with claim 1 further comprising:

first sealing means located adjacent said input port for sealing said input port of said closed container prior to use to prevent anything from entering or exiting said closed container via said input port, said first sealing means is capable of opening said input port during use of said decontamination apparatus to permit waste matter and suction air flow to enter said closed container; and second sealing means located adjacent said exhaust port for sealing said exhaust port of said closed container prior to use to collect said waste matter in order to prevent anything from entering or exiting said closed container via said exhaust port, said second sealing means is capable of opening said exhaust port during use of said decontamination apparatus to permit said sterilized suction air flow to exit said closed container.

8. The decontamination apparatus in accordance with claim 7 wherein:

said first sealing means comprises a first membrane sealing said input port, and a first pointed member which is capable of rupturing said first membrane to allow said waste matter and said suction air flow to enter said closed container; and said second sealing means comprises a second membrane sealing said exhaust port, and a second pointed member which is capable of said second membrane to allow said sterilized suction air flow to exit said closed container.

9. The decontamination apparatus in accordance with claim 1 further comprising:

actuation means located in said closed container for bringing said first disinfectant means into contact with said waste matter collected in said closed container to disinfect same before said closed waste container is disposed of.

10. The decontamination apparatus in accordance with claim 9 wherein said first disinfectant means comprises a first disinfectant bath, and further comprising:

a tank for containing said first disinfectant bath, said tank having a drain that is capable of opening when said closed container is full of waste matter to drain said first disinfectant bath into said collected waste matter to sterilize same.

11. The decontamination apparatus in accordance with claim 10 further comprising:

a pipe means in the bottom of said tank means through which said suction air flow passes when said suction source is connected to said exhaust port and said suction pickup device is connected to said input port, said pipe means having an end open to said closed container above said collected waste matter, and having at least one exit port through which suction air flow passes into said first disinfectant bath to initially be broken up into a first plurality of bubbles; and screen means above said pipe means through which said first plurality of bubbles passes to be broken up into a larger number of fine bubbles, said pipe means and said screen means being located in said first disinfectant bath, thereby permitting said larger number of fine bubbles to pass up through said first disinfectant bath to sterilize said suction air flow.

12. A method for sterilizing suction air created by a suction source used to pick up waste matter, and before the suction air is exhausted into the surrounding environment, said method comprising the steps of:

passing contaminated suction air through a closed container where waste matter is collected;

passing said contaminated suction air through a disinfectant means to sterilize said contaminated suction air after said waste matter has been collected in said closed container prior to said contaminated suction air entering a suction source; and contacting said waste matter with said disinfectant means to sterilize said waste matter when said closed container is full of said waste matter and is to be disposed of.

13. The method in accordance with claim 12 wherein said disinfectant means comprises a disinfectant bath and further comprising the step of:

passing said contaminated suction air through said disinfectant bath to disinfect said contaminated suction air.

14. The method in accordance with claim 13 further comprising the step of:

passing said disinfected suction air through a filter to remove any particulate matter and odors from it before it is exhausted to the surrounding environment.

15. The method in accordance with claim 14 further comprising the step of:

draining said disinfectant bath into said closed container when said container is full of waste matter to disinfect said waste matter collected in said closed container.

16. The method in accordance with claim 13 wherein said step of passing said contaminated suction air through said disinfectant bath comprises the step of:

breaking said contaminated suction air up into a large plurality of bubbles to pass through said disinfectant bath.

17. The method in accordance with claim 16 wherein said contaminated suction air enters said closed container via an input port and the disinfected suction air exists said closed container via an exhaust port, and further comprising the steps of:

allowing said contaminated suction air to enter said closed container via said input port while blocking anything from exiting said closed container via said input port, and permitting said disinfected suction air to exit said closed container via said exhaust port while blocking anything from entering said closed container via said exhaust port.

18. The method in accordance with claim 17 further comprising the steps of:
sealing said input port of said closed container before it is used to collect waste matter; and
breaking said seal to allow waste matter to be drawn into said closed container using suction air.

19. The method in accordance with claim 18 further comprising the steps of:
sealing said exhaust port of said closed container before it is used to collect waste matter; and
breaking said seal when said closed container is to be used, thereby permitting said disinfected suction air to exit said closed container via said exhaust port.

20. In a decontamination apparatus used with a suction source which creates suction that causes suction air flow into a suction pickup device to pick up waste matter which is deposited in said decontamination apparatus before said suction air flow is exhausted into the surrounding environment, the improvement comprising:
a closed container having an input port and an exhaust port, said exhaust port being connected to said suction source and said suction pickup device being connected to said input port, said suction air flow entering said closed container via said suction pickup device and said input port and exiting said closed container via said exhaust port, said closed container collects said waste matter that is drawn into said closed container by said suction air flow created by said suction source;
a first disinfectant means through which said suction air flow passes after said suction air flow enters said closed container to separate said waste matter from said suction air flow, said first disinfectant means for sterilizing said suction air flow passing through said closed container via said input port and said exhaust port prior to entering said suction source; and
a porous medium located inside of said closed container adjacent to said exhaust port, said porous medium being impregnated with said first disinfectant means, and wherein said suction air flow is sterilized when passed through said porous medium contacting said first disinfectant means.

21. The invention in accordance with claim 20 further comprising:
a second disinfectant means for disinfecting said waste matter collected in said closed container before said container is disposed of.

22. The invention in accordance with claim 21 further comprising:
a tank for containing said second disinfectant means, said tank having a drain that is capable of opening when said closed container is full of waste matter to drain said second disinfectant means into said collected waste matter to sterilize same.

23. In a decontamination apparatus used with a suction source which creates suction that causes an suction air flow into a suction pickup device to pick up waste matter which is then deposited in said decontamination apparatus before said suction air flow is exhausted into the surrounding environment, the improvement comprising:
a closed container having an input port and an exhaust port, said exhaust port being connected to said suction source and said suction pickup device being connected to said input port, said closed container collects a waste matter that is drawn into said closed container by said air flow created by said suction source;
a porous medium adjacent to said exhaust port and through which said suction air flow passes after said waste matter is separated from said suction air flow; and
a means for heating said porous medium to sterilize said suction air flow passing through said porous medium.

24. The decontamination apparatus in accordance with claim 23 further comprising:
a disinfectant means for disinfecting said waste matter collected in said closed container before said closed container is disposed of.

25. The invention in accordance with claim 24 further comprising:
a tank for containing said disinfectant means, said tank having a drain that is capable of opening when said closed container is full of waste matter to drain said disinfectant means into said collected waste matter to sterilize same.

* * * * *